United States Patent
Dunn (10) Patent No.: US 8,409,231 B2
(45) Date of Patent: Apr. 2, 2013

(54) SCALPEL HANDLE

(75) Inventor: Raymond Dunn, Shrewsbury, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 12/765,603

(22) Filed: Apr. 22, 2010

(65) Prior Publication Data

US 2010/0324577 A1 Dec. 23, 2010

Related U.S. Application Data

(63) Continuation-in-part of application No. 11/662,716, filed as application No. PCT/US2005/032416 on Sep. 13, 2005.

(60) Provisional application No. 60/609,430, filed on Sep. 13, 2004.

(51) Int. Cl.
A61B 17/32 (2006.01)

(52) U.S. Cl. ............ 606/167; 606/181; 30/340; 30/329

(58) Field of Classification Search .................. 606/167, 606/172, 185, 166, 159, 181; 30/329–344
See application file for complete search history.

(56) References Cited

U.S. PATENT DOCUMENTS

| | | | | |
|---|---|---|---|---|
| 1,037,802 | A * | 9/1912 | Smith | 606/181 |
| 3,187,431 | A | 6/1965 | Mattes | |
| 4,327,465 | A | 5/1982 | Moritsch | |
| 4,576,164 | A | 3/1986 | Richeson | |
| 4,631,052 | A | 12/1986 | Kensey | |
| 4,679,558 | A | 7/1987 | Kensey et al. | |
| 4,739,536 | A * | 4/1988 | Bandera et al. | 16/430 |
| 4,759,363 | A | 7/1988 | Jensen | |
| 4,798,000 | A | 1/1989 | Bedner et al. | |
| 4,844,070 | A | 7/1989 | Dee | |
| 4,846,250 | A | 7/1989 | Bedner et al. | |
| 4,959,067 | A * | 9/1990 | Muller | 606/190 |
| 4,974,286 | A * | 12/1990 | Stowell et al. | 16/421 |
| 5,100,391 | A * | 3/1992 | Schutte et al. | 606/167 |
| 5,312,429 | A | 5/1994 | Noack | |
| 5,344,424 | A | 9/1994 | Roberts et al. | |
| 5,417,704 | A | 5/1995 | Wonderley | |
| 5,556,092 | A * | 9/1996 | Theken | 473/538 |
| 5,578,050 | A * | 11/1996 | Webb | 606/167 |
| 5,868,771 | A * | 2/1999 | Herbert et al. | 606/167 |
| 5,919,201 | A | 7/1999 | Carter et al. | |
| 5,938,675 | A | 8/1999 | Gharibian | |
| 5,938,676 | A | 8/1999 | Cohn et al. | |
| 5,941,892 | A | 8/1999 | Cohn et al. | |
| 6,053,929 | A | 4/2000 | Cohn et al. | |
| 6,645,216 | B2 | 11/2003 | Masury et al. | |
| 6,884,240 | B1 | 4/2005 | Dykes | |
| 7,207,999 | B2 | 4/2007 | Griffin et al. | |
| 7,306,615 | B2 | 12/2007 | Wilson | |
| 7,387,637 | B2 | 6/2008 | Morawski et al. | |
| 2003/0233780 | A1 * | 12/2003 | Grieco | 43/22 |
| 2006/0041266 | A1 | 2/2006 | Sullivan et al. | |
| 2006/0100650 | A1 | 5/2006 | Kiehne | |
| 2007/0156160 | A1 | 7/2007 | Petersen | |

* cited by examiner

Primary Examiner — Ryan Severson
Assistant Examiner — Tin Nguyen
(74) Attorney, Agent, or Firm — McCarter & English, LLP (57) ABSTRACT

The present invention relates to a contoured scalpel handle. The contoured shape of the handle provides for increased contact area with the user's hand using a larger diameter central portion and a smaller diameter trough. The generally circular cross-section allows rotation of the angle of the blade relative to the tissue without the need to change the grip on the handle. The contoured handle can be used as an adapter sleeve in which a scalpel handle can be inserted or can include a blade mounting element on which a blade is directly mounted.

24 Claims, 8 Drawing Sheets

SCALPEL HANDLE

CROSS REFERENCE TO RELATED APPLICATIONS

This is a continuation-in-part application of U.S. application Ser. No. 11/662,716 filed on Mar. 13, 2007, which is a U.S. National Phase Application of International Application No. PCT/US05/032416 filed on Sep. 13, 2005, which claims the benefit under 35 U.S.C. 119(e) of U.S. Provisional Application No. 60/609,430, filed Sep. 13, 2004, the disclosure of the above referenced application being incorporated herein by reference.

BACKGROUND OF THE INVENTION

Surgeons have traditionally used scalpels for a variety of surgical procedures to cut or excise tissue. Surgical precision requires, in certain types of procedures, the angle of orientation of the scalpel blade to be of particular importance.

For example, each year many people have skin growths, such as moles, removed. In order to excise the mole the surgeon must use a scalpel to make two mirror image incisions in the skin around the mole. Depending on the "handedness" of the surgeon one incision is more difficult to make than the other. This is due to the traditional flat handle design used for most scalpels, which makes it much harder to hold the blade in the proper fashion. The flat handle requires the surgeon's wrist to roll more for one incision versus the other, thus increasing the chance of a minor hand tremor or misalignment of the blade relative to the surgical site while cutting. This in turn, reduces the precision with which minor image symmetry can be created.

Thus, there is an ongoing need for improvements in scalpel design to facilitate greater ease in surgical applications.

SUMMARY OF THE INVENTION

The present invention relates to scalpel handle devices having a handle geometry suitable for more complex incisions common in many surgical procedures. Many of these procedures require the surgeon to hold the scalpel handle differently in order to cut at different angles or along curves.

A preferred embodiment of the invention uses a contoured handle having a generally circular cross-section along its longitudinal length. This shape enables the surgeon to freely rotate the scalpel blade to different angles to reduce the need to hold the handle differently. The handle has a double trough shape where the central portion of the handle has a larger diameter and is positioned centrally relative to two narrower diameter regions or troughs that are contoured for manual grasping by the surgeon.

This present invention further relates to an adapter sleeve that can be attached to a scalpel blade. The adapter sleeve provides a handle that is easier to hold, thereby giving the surgeon greater control and ability to make more precise incisions. The adapter sleeve of the present invention includes a cavity extending through a portion of the sleeve that receives the proximal end or handle of the scalpel such that the blade extends from the distal end of the adapter. An outer surface region of the adapter sleeve includes a handle portion that is gripped manually by the hand of the user during a surgical procedure. The sleeve handle has a contoured surface to provide for proper orientation of the blade of the scalpel relative to the surgical site. The contoured surface of the handle can include a proximal section with a thicker diameter that tapers to a smaller diameter section at the distal end. The distal section can have a recess for the thumb of the user. The blade can be rigidly oriented relative to the surface features to improve manual manipulation. The sleeve handle can be left or right handed.

In accordance with a preferred embodiment, the method for using the adapter sleeve of the present invention involves selecting a blade, inserting it into the adapter, performing the selected procedure, removing the scalpel for cleaning, sterilization, and reuse, and either sterilizing or disposing of the adapter sleeve.

In another preferred embodiment, the scalpel blade is assembled with the adapter sleeve during manufacture. The adapter sleeve in this embodiment is made of a plastic material suitable for sterilization after use. The sleeve can be molded as a unitary body with selected portions of the surface having a hatched, a braided or dimpled surface to provide frictional surface regions unlikely to slip when grasped by the user. The sleeve can also be molded in two pieces that snap together about the blade using a connector.

A preferred embodiment can also include a rotational mechanism to provide for adjustment of the angular orientation of the blade relative to the adapter handle. In one example, the cavity is sized to provide for two different angular orientation of the blade edge relative to the adapter handle, thus allowing the user to select the proper orientation for a given procedure. In a second example, the adapter handle call have inner and outer sections or sleeves that rotate relative to each other. The user can turn the blade relative to the handle which "clicks" between selectable rotational positions to find that most suitable.

The scalpel handle can be manufactured using an injection molding process. A molded plastic material is used and can be adapted for single use (disposable), or alternatively, manufactured using a material suitable for sterilization procedures for reuse. The scalpel handle can be color coded such that the color can indicate a particular size and/or type of blade for the type of procedure.

The foregoing and other features and advantages of the system and method for a scalpel adapter sleeve will be apparent from the following more particular description of preferred embodiments of the system and method as illustrated in the accompanying drawings in which like reference characters refer to the same parts through out the different views.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

This invention describes an adapter sleeve that can be attached to existing flat handled scalpels. The adapter sleeve can be elliptical in shape at least along a portion thereof and crosshatched or beveled to make the handle a more natural feel thereby making it easier to hold to provide superior scalpel manipulations. In addition, the design can also be manufactured as a knife handle unit.

The adapter sleeve can be a sterilizable or disposable, elliptical-shaped, beveled plastic handle that can be used on existing scalpel handles. In addition to making the handle of the scalpel easier to hold, the design of the adapter also has the advantage of making the handle less slippery than the traditional steel handle. Through use of the adapter sleeve the scalpel will be easier to manipulate thereby allowing the precision of the incision to be increased.

Figure 1:
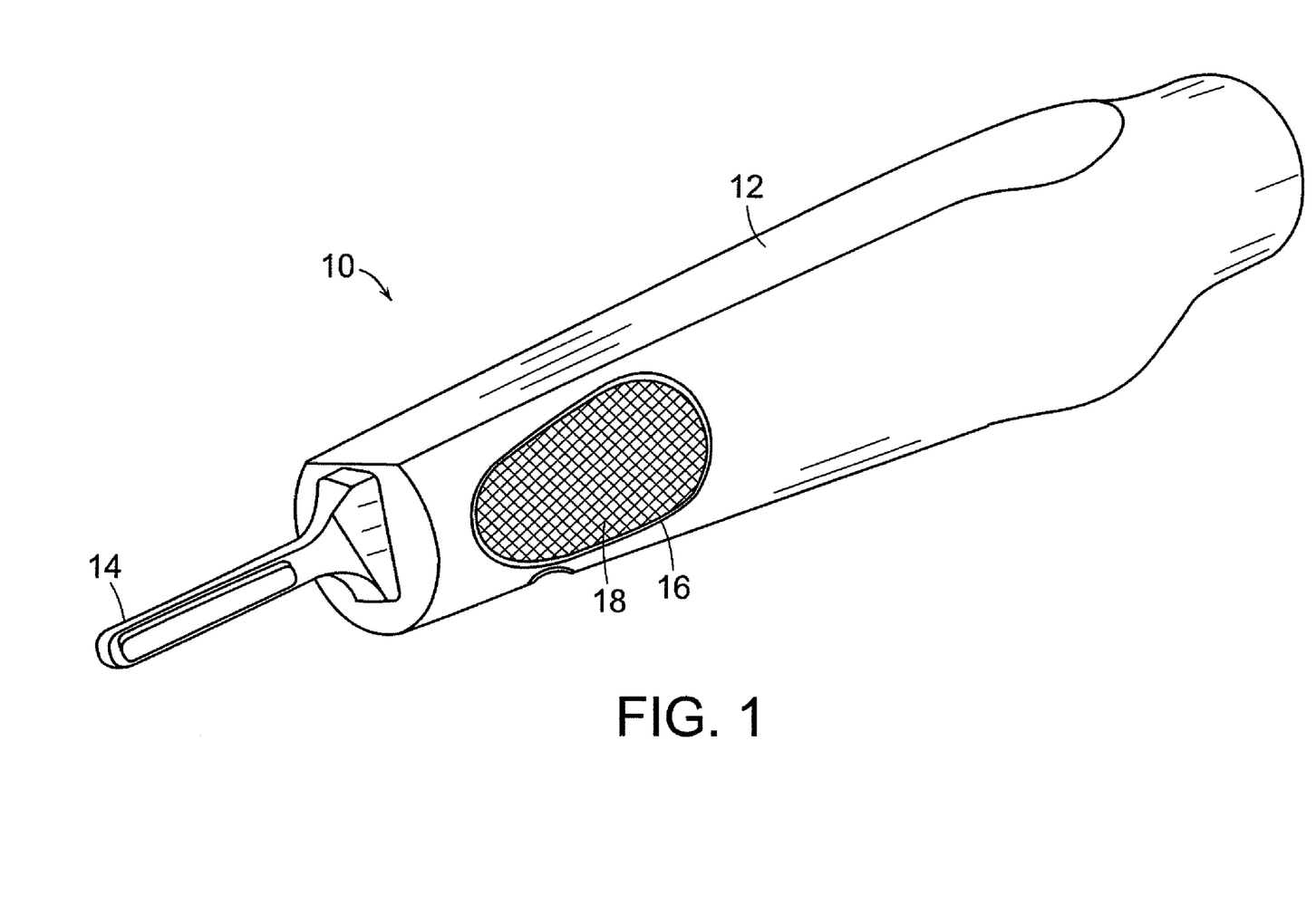
FIG. 1 is a front side perspective view of the adapter sleeve with a scalpel blade inserted therein in accordance with a preferred embodiment of the present invention.

A preferred embodiment of the invention is illustrated in connection with FIG. 1. The adapter sleeve scalpel device 10 of this embodiment has a contoured handle 12 and a distally mounted blade 14 that is rigidly attached to the handle. A front side of the handle 12 is shown with a recess 16 sized to receive the thumb of a user. The recess can be a hatched, abraded, or provided with some other frictionally enhanced surface region 18 to improve gripping and manual manipulation of the blade.

Figure 2:
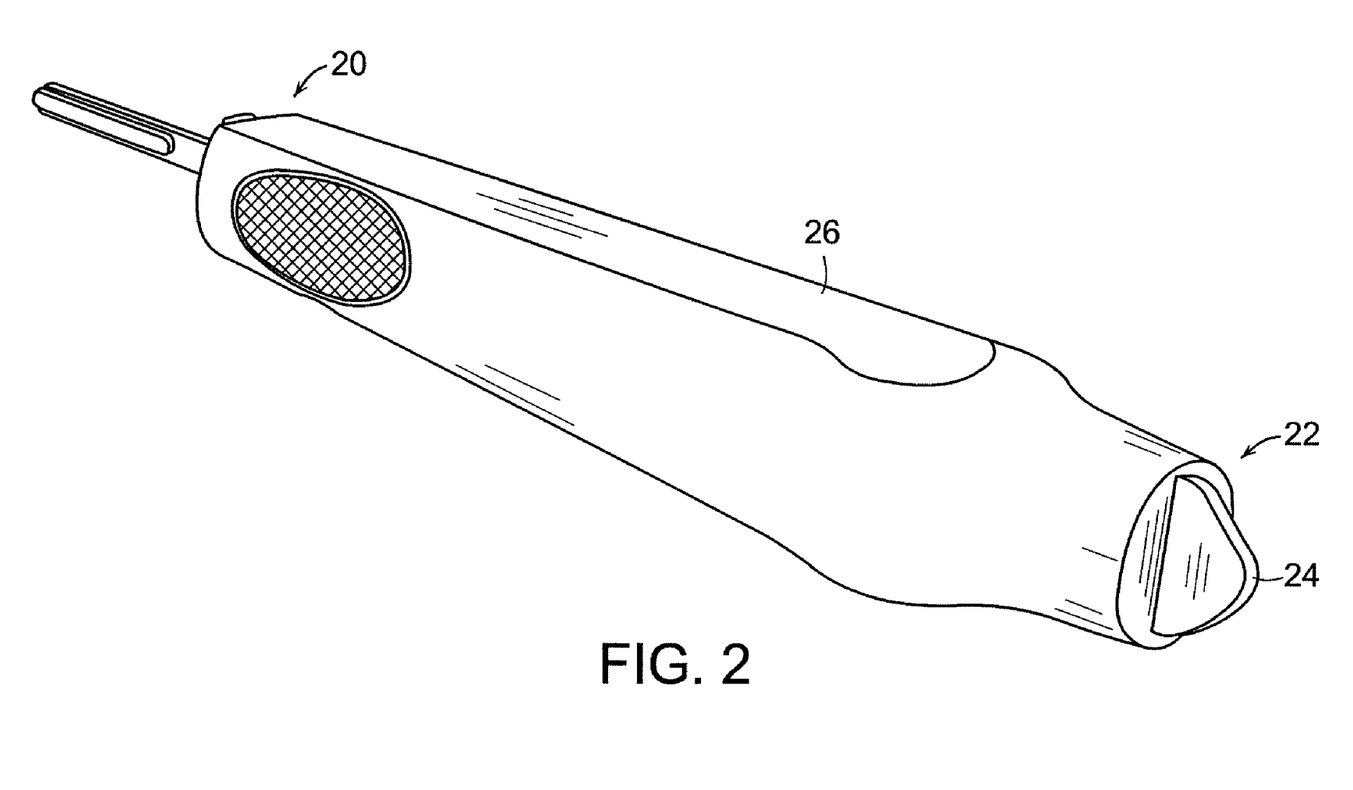
FIG. 2 is a perspective view of the proximal end of the device seen in FIG. 1 in accordance with a preferred embodiment of the present invention.

A rear perspective view of an adapter sleeve and scalpel is shown in FIG. 2. The adapter handle has a distal portion 20, a proximal portion 22, and a lateral side 26 which has a flattened portion in this embodiment. A proximal end 24 of the scalpel blade can extend from proximal portion 22.

Figures 3, 4:
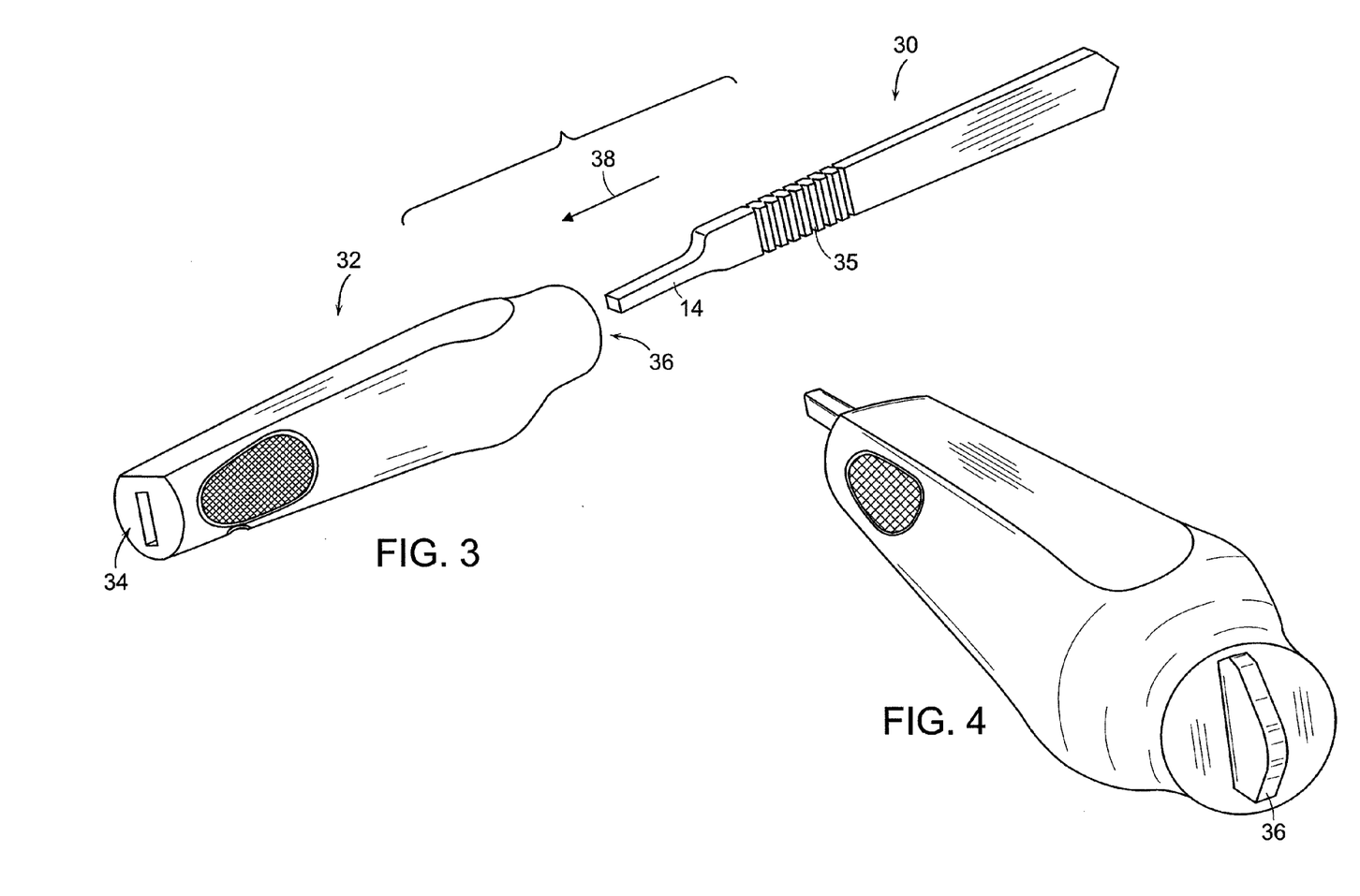
FIG. 3 is a perspective view of the adapter sleeve with a scalpel blade positioned for insertion at the proximal end of the adapter in accordance with a preferred embodiment of the present invention.
FIG. 4 is a perspective view of the proximal end of the adapter and scalpel in accordance with a preferred embodiment of the present invention.

In the embodiment illustrated in FIG. 3, the distal end 14, of scalpel 30 is inserted in direction 38 into a proximal cavity opening 36 of the adapter sleeve 32. The scalpel blade slides through the cavity until the blade extends through the distal cavity or channel opening 34 of the adapter. The inner cavity surface is shaped to conform to the shape of the scalpel blade to securely grip the blade during use. The inner surface of the cavity, can also be scalloped or dimpled to engage the frictional surface features 35 of the scalpel handle. Alternatively, the adapter handle can be fitted with a "snap" feature that locks the scalpel handle in place upon insertion. FIG. 4 shows a rear perspective view of the embodiment in FIG. 3 with the scalpel inserted into proximal opening 36.

Figure 5:
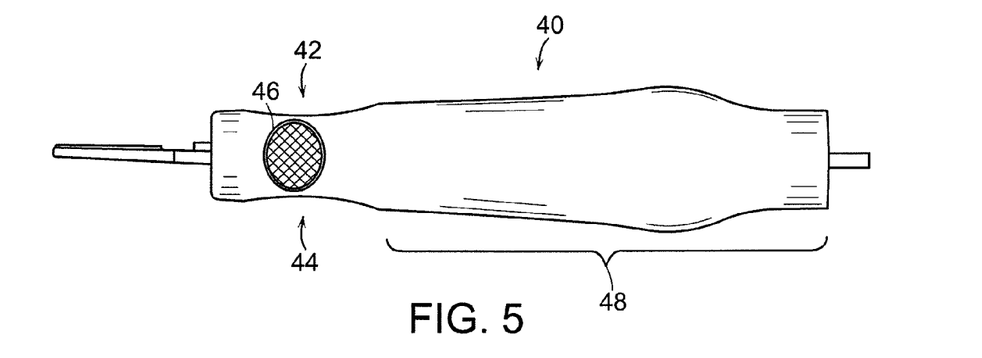
FIG. 5 is a rear side view of the adapter and scalpel in accordance with a preferred embodiment of the present invention.

A preferred embodiment of the invention illustrated in FIG. 5 shows a side view, in which the proximal portion 48 of adapter 40 has a circular or elliptical cross-sectional shape. The front and rear sides of adapter 40 have recesses 42 and 44, respectively, that can be gripped by the thumb and fingers of the user. Additionally, one or both lateral sides can have smaller recess 46.

Figure 6:
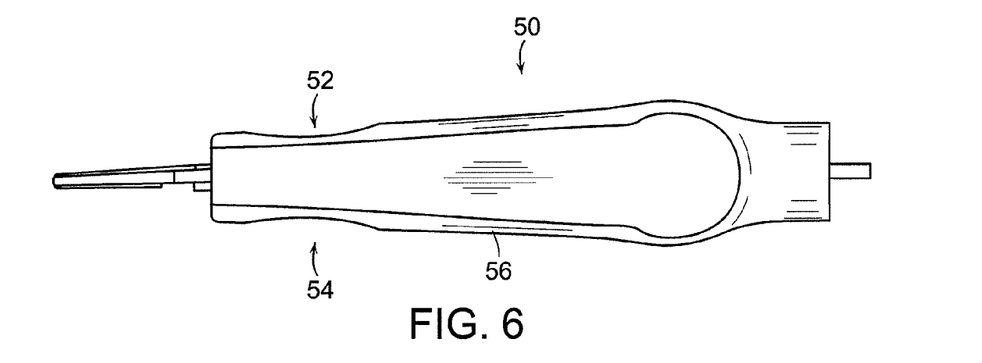
FIG. 6 is a lateral side view of the adapter sleeve and scalpel in accordance with a preferred embodiment of the present invention.

In the embodiment illustrated in FIG. 6, the adapter has front and rear recesses 52 and 54, respectively, however, the lateral sides have flattened regions 56. The features illustrated in FIGS. 5 and 6 give the user a positive feel for how the blade of the scalpel is oriented relative to the surgical sites.

Figure 7:
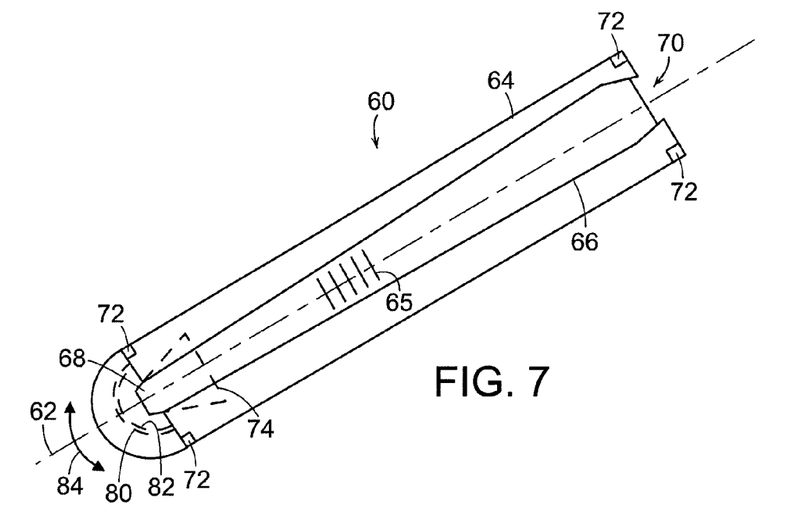
FIG. 7 is a cross-section view illustrating an internal cavity that receives scalpel blade in accordance with a preferred embodiment of the present invention.

A cross-sectional view of an adapter handle 60 is shown in FIG. 7. In a preferred embodiment, the adapter 60 is made of a solid unitary element 64, in which a cavity 66 extends along a longitudinal axis 62. The cavity 66 can be shaped to conform to a handle of a scalpel blade such as that shown at 30 in FIG. 3. The user, as described previously herein, inserts the distal end 14 of the blade through the proximal opening 70 until the blade 14 extends through the distal opening 68. The interior surface of the cavity can have a fractional surface such as ridges 65 that engage surface features 35 (FIG. 3) of the blade handle. In an embodiment in which the adapter handle has two sections, connector 72 can be used to connect the two portions together.

In another preferred embodiment, the scalpel blade has a blade section and a proximal section that mates with the internal cavity 74 shown in outline in FIG. 7. In this embodiment, the cavity does not extend through the length of the handle 64. Rather, The proximal section of the blade fits snugly within distal cavity 74 and the proximal section of the handle can be a solid material.

A preferred embodiment of the invention can employ the option of providing different angular orientations of the blade relative to the adapter handle. The different positions can be over a continuous range of angular position 84 between 0-180 degrees, or they can be discrete. In one embodiment, the cavity can be sized in a manner allowing for two discrete angular positions in which the blade can be inserted. In another embodiment, the adapter 60 can fuclude an outer sleeve adapter section that fits at cylindrical surface 80 relative to an inner sleeve or section that nests at cylindrical surface 82 with the outer section. The two sections rotate 84 relative to each other such that the user can adjust between angular orientations of the blade relative to the adapter. The user can-select between discrete angular orientations in which the user can "click" between fixed angular positions that are, for example, 10-30 degrees apart.

Figure 8A:
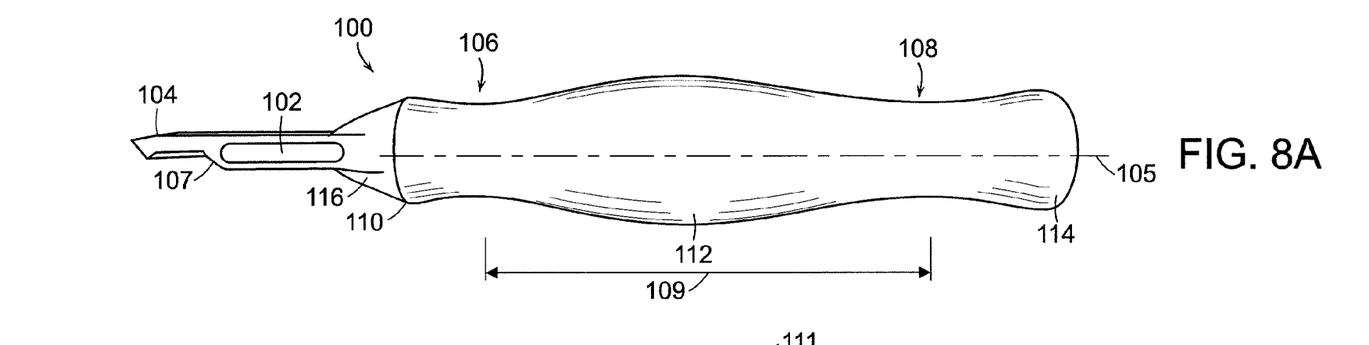
FIGS. 8A-8D illustrate views of a scalpel handle in accordance with a preferred embodiment of the invention.

A preferred embodiment of a scalpel handle is shown in connection with FIGS. 8A-8D. As shown in FIG. 8A, a scalpel handle 100 includes a handle portion divided into a distal portion 110, a central portion 112 and a proximal portion 114. Between the distal and central portions is a first concave section 106 or trough adapted to be grasped by the thumb/forefinger and middle finger of the user. Between the central portion and the proximal portion is a second concave section 108 or trough adapted to rest in the web of the user's hand between the thumb and forefinger. A tapered section 116 extends from the distal portion 110 of the handle to a blade mounting element 102.

The dimensions of the handle portions are selected to provide for precision and control of the blade during use as well as comfort of the user. The dimensions of the handle features are also of importance as they maximize contact surface area to improve tactile feels of the handle in the user's hand. A common grip of the scalpel is the pencil grip where the thumb, forefinger and middle finger of the user's hand provide three points of contact in the first trough section. In a preferred embodiment, this first trough 106 has a circular cross-section with a minimum diameter in a range of 1.0 to 1.5 cm, preferably about 1.3 cm. In a distal direction from the trough 106, the diameter of the handle increases to prevent the fingers from sliding distally toward the blade mounted on the distal end, particularly when more force is exerted in a distal direction. The larger diameter distal portion 110 has a flared diameter in a range of 1.2 to 1.8 cm, preferably about 1.5 cm. The central portion 112 has a diameter in a range of 1.6 to 2.4 cm in diameter, preferably about 1.9 cm. The larger central portion increases the area of contact with the fingers to further stabilize the device in the user's hand. The second trough 108 has a diameter in a range of 1.0 to 1.5 cm, preferably about 1.3 cm. The second trough fits within the web extending between the user's thumb and forefinger. The proximal portion 114 is flared, with a diameter in a range of 1.5 to 2.0 cm, preferably between 1.7 and 1.8 cm.

These diameter dimensions are correlated with the longitudinal distance between features to achieve the described fit to the surgeon's hands. The distance 109 between the minimum trough diameters is in a range of 6.4 cm to 7.2 cm, preferably about 6.8 cm. The distance 111 from the distal end of the taper to the proximal end of the handle is in a range of 12 to 14 cm, preferably around 12.5 to 13.2 cm. The length of the device is in a range of 14.0 cm to 15 cm.

Precise control of the blade during use is critical. If the handle is awkward to hold, this can contribute to the difficulty of the procedure by compelling the surgeon to awkwardly grasp the tool to achieve the proper angle and level of force required to cut the tissue as needed. Thus, proper balance, good contact between the user's hand and the handle, and the ability to rotate the handle without having to grip the tool differently can be of great importance.

Figure 8B:
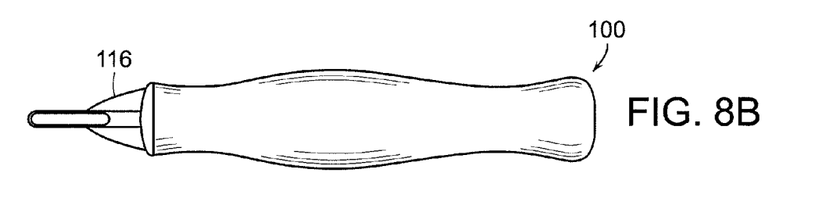
Figure 8C:
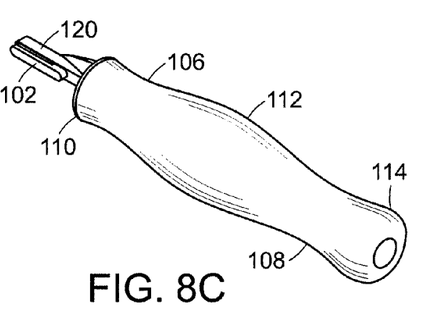
Figure 8D:
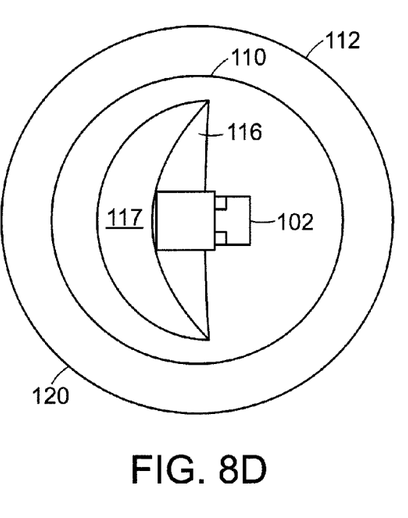

As shown in FIGS. 8B and 8C the tapered region 116 extends to a rigid post 120 situated along the central longitudinal axis 105 of the handle from which the mounting element 102 extends. The mounting element has a length, width and depth adapted for insertion within a standard blade slot 107. FIG. 8D shows an enlarged end view of the distal end of the handle 100.

Figure 9:
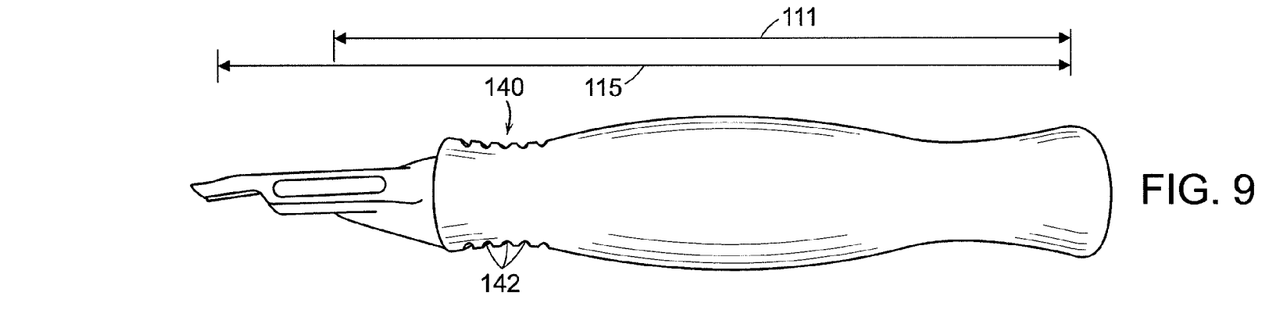
FIG. 9 illustrates a handle having a textured region to enhance grasping by the thumb and forefinger of the user.

Shown in FIG. 9 is another preferred embodiment of a scalpel handle in which a textured region 140 comprising a plurality of ribs 142 extending circumferentially around the longitudinal axis of the handle. The textured region enhances the friction with the user's hand.

FIGS. 10A-10D illustrate a preferred embodiment of a scalpel handle 150 having an angled proximal portion 158, a wider diameter central portion 156, a distal transition region 154 extending to a post 152 situated along the longitudinal axis 155. This embodiment is slightly elliptical or oval in cross-sectional shape with a wider diameter (up to 30 percent larger) in the plane of the blade. The slightly elliptical shape accommodates rotation of the blade but gives the user a tactile feel for angular orientation of the blade. The angled portion 158 extends along a second axis 157 at angle 160 relative to axis 155.

Figure 10A:
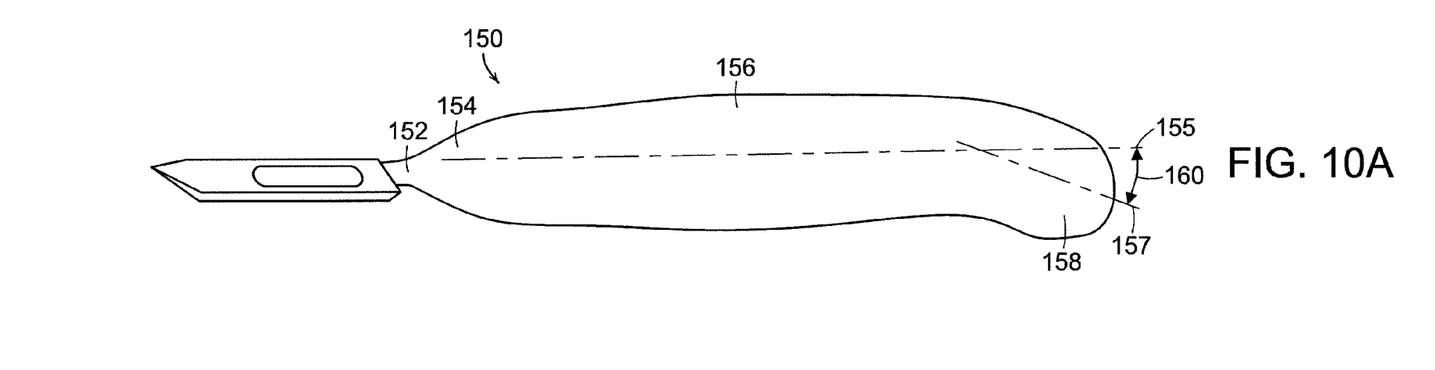
FIGS. 10A-10D illustrate views of a preferred embodiment of a scalpel handle in accordance with the invention.
Figure 10B:
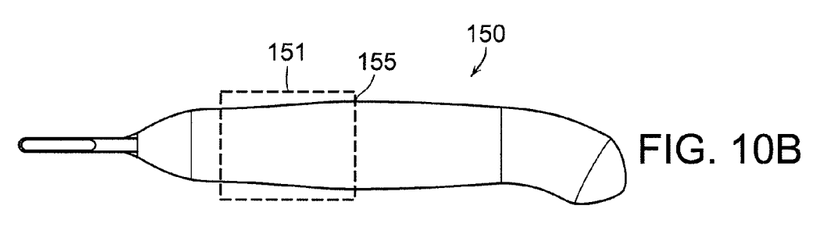
Figure 10C:
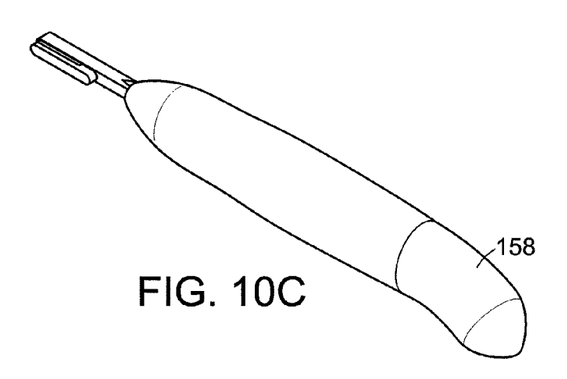
Figure 10D:
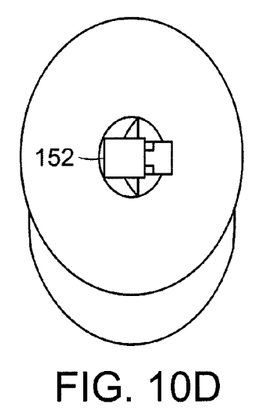

The handles of the various embodiments of the present invention can include a sleeve 151 to enhance the grasp of the user. Such a sleeve 151 is replaceable and can be used with any of the embodiments of the invention described herein. The sleeve can be used to alter the shape and texture of the handle. The sleeve 151 can be an elastic material that can be replaced when worn or if a different shape, color or texture is needed for a particular procedure. The sleeve can slide onto the handle. Alternatively, the sleeve 151 can fit within a recess 155 on the outer surface of the handle.

Figure 13A:
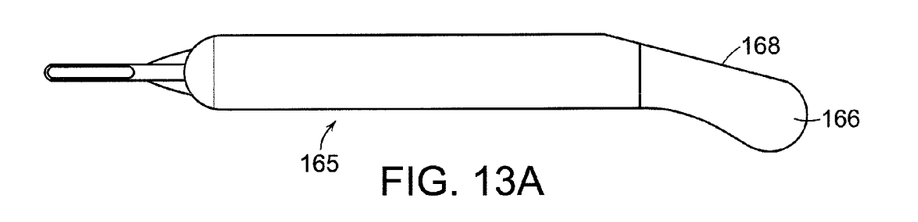
FIGS. 13A-13C illustrate views of a preferred embodiment of a scalpel handle in accordance with the invention.
Figure 13B:
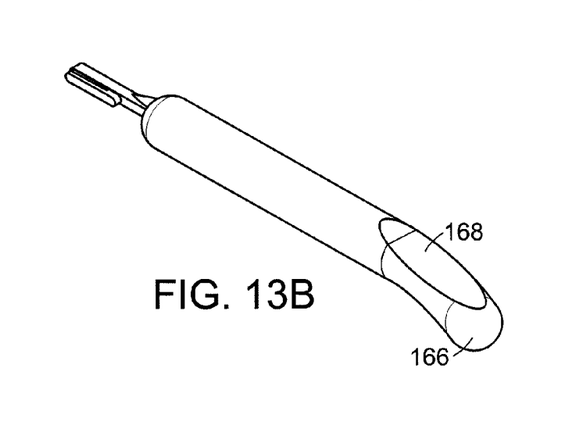
Figure 13C:
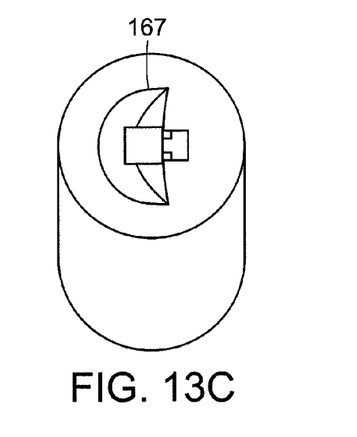

As seen in the embodiment of FIGS. 13A-13C, the scalpel handle 165 can have a flattened region 168 opposite the angled portion 166 and a larger diameter transition 167. This also uses a generally cylindrical shape.

Figure 11A:
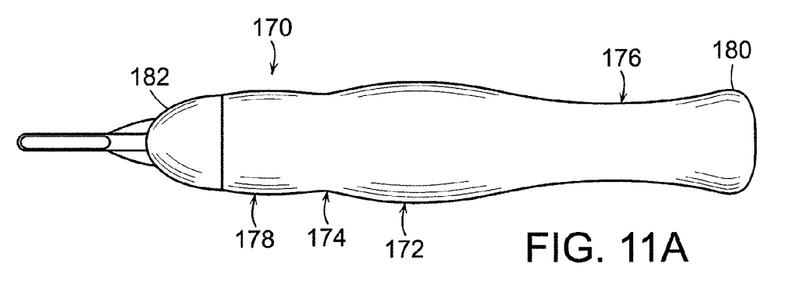
FIGS. 11A-11C illustrate views of a preferred embodiment of a scalpel handle in accordance with the invention.
Figure 11B:
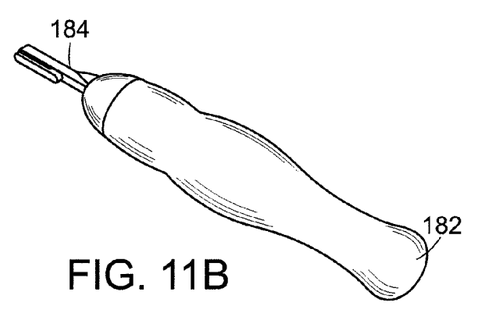
Figure 11C:
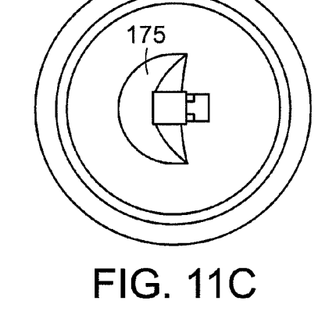

FIGS. 11A-11C show a further embodiment 170 having a larger diameter central portion 172 having the dimensions previously described with a distal trough 174, a proximal trough 176, a flared proximal end 180, a semi-conical tapered portion 175 extending to post 184. This embodiment has an enlarged distal diameter region 178 and a distal conical section 182.

Note that the embodiments of FIGS. 8A-14C can also be manufactured as adapter sleeves for a standard flat handled scalpel, which can be inserted through a proximal opening, such as 182 shown in FIG. 11B.

Figure 12A:
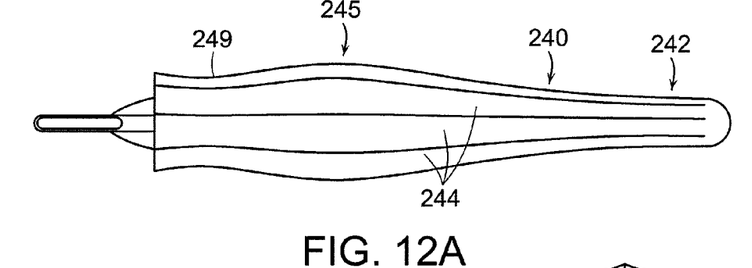
FIGS. 12A-12C illustrate views of a preferred embodiment of a scalpel handle in accordance with the invention.
Figure 12B:
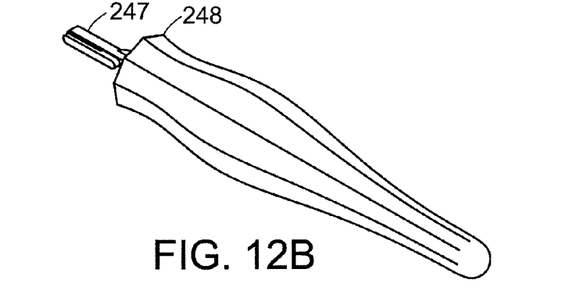
Figure 12C:
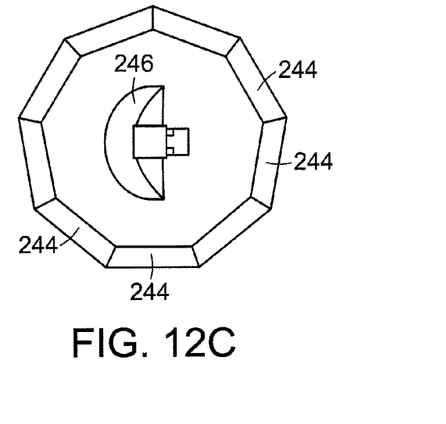

A preferred embodiment is illustrated in FIGS. 12A-12C in which scalpel handle 240 has flattened section 244 extending along the length of the handle. A larger diameter central section 245 has a distal trough 249, a narrow diameter proximal section 242 and a flared distal section. A semi-conical taper 246 extends to the post 247.

Figure 14A:
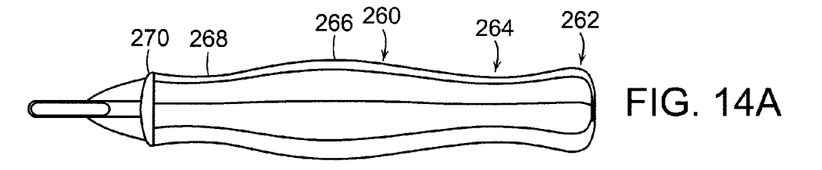
FIGS. 14A-14C illustrate views of a preferred embodiment of a scalpel handle in accordance with the invention.
Figure 14B:
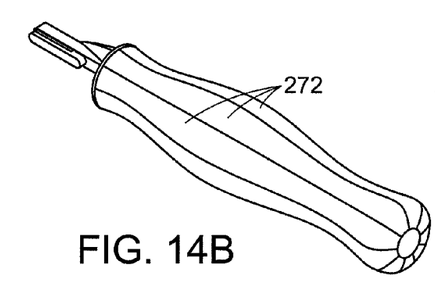
Figure 14C:
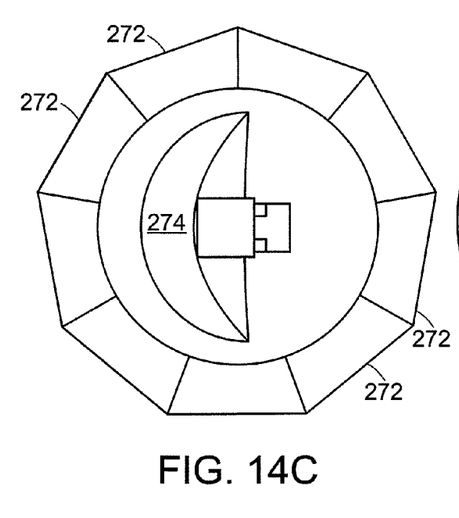

Shown in FIGS. 14A-14C is an embodiment of a handle 260 having flattened sections 272, troughs 264 and 268, flared proximal 262, and distal 270 sections and a larger diameter central section 266. This embodiment has a larger tape 274 to the post. The flattened sections 244, 272 give the user better tactile feels of the degree of rotation without inhibiting use at numerous angles. There are preferably between 6 and 12 separate surfaces extending around the perimeter.

The claims should not be read as limited to the described order or elements unless stated to that effect. Therefore, all embodiments that come within the scope and spirit of the following claims and equivalents thereto are claimed as the invention.

What is claimed is:

1. A surgical scalpel handle comprising:
   a surgical scalpel handle having a contoured handle surface to be held in a hand of a user, the contoured handle surface having a distal trough, a larger diameter central portion having a circular cross-section and a proximal trough extending about a longitudinal axis of the scalpel handle; and
   a surgical blade mounting element adapted to receive a surgical blade that is mountable on the mounting element, the mounting element being positioned on a post that extends from a distal end of the scalpel handle such that the user can rotate the scalpel handle in the user's hand to rotate the mounted surgical blade during cutting of tissue.

2. The scalpel handle of claim 1 wherein the blade mounting element extends laterally from the post.

3. The scalpel handle of claim 1 wherein the contoured handle surface comprises a proximal portion having an elliptical shape.

4. The scalpel handle of claim 1 wherein the contoured handle surface comprises a distal portion with a recess for a sleeve.

5. The scalpel handle of claim 4 wherein the sleeve comprises an elastic material removable from the handle.

6. The scalpel handle of claim 1 wherein the contoured handle surface has a flared proximal portion.

7. The scalpel handle of claim 2 wherein the post extends from a distal tapered section.

8. The scalpel handle of claim 1 wherein the handle surface has a frictional portion to be engaged by a finger of the user.

9. The scalpel handle of claim 1 wherein the blade mounting element is adapted to be inserted into a blade slot.

10. The scalpel handle of claim 1 wherein the handle comprises a molded plastic material.

11. The scalpel handle of claim 1 wherein the handle comprises a flared distal portion.

12. The scalpel handle of claim 1 wherein the distal trough has a diameter in a range of 1.0 cm to 1.5 cm.

13. The scalpel handle of claim 1 wherein the handle has a length between the distal trough and the proximal trough in a range of 6.4 cm to 7.2 cm.

14. The scalpel handle of claim 1 wherein the larger diameter central portion has a diameter in a range of 1.6 cm to 2.4 cm.

15. The scalpel handle of claim 1 further comprising the surgical blade having a slot such that the surgical blade can be mounted onto the mounting element with the slot.

16. A surgical scalpel handle comprising:
a surgical scalpel handle having a longitudinal axis and a contoured handle surface to be held in a hand of a user, the contoured handle surface having a distal flare, a distal trough, a larger diameter central portion having a circular cross-section and a proximal trough that extend about the longitudinal axis; and
a surgical blade mounting element positioned on a post extending along the longitudinal axis from a distal end of the surgical scalpel handle, the surgical blade mounting element being adapted to receive a surgical blade that is mountable on the mounting element such that the user can rotate the handle in the user's hand to rotate the mounted surgical blade during cutting of tissue.

17. The scalpel handle of claim 16 wherein the contoured handle has a recess.

18. The scalpel handle of claim 16 wherein the contoured handle has a flared proximal portion.

19. The scalpel handle of claim 16 wherein the handle comprises a unitary molded plastic material.

20. The scalpel handle of claim 16 wherein the larger diameter central portion has a diameter in a range of 1.6 cm to 2.4 cm.

21. The scalpel handle of claim 16 further comprising a sleeve positioned in the distal trough.

22. The scalpel handle of claim 16 wherein the contoured handle surface further comprises an oval portion.

23. The scalpel handle of claim 16 wherein the handle can have a plurality of colors.

24. The scalpel handle of claim 16 further comprising the surgical blade having a slot such that the surgical blade can be mounted onto the mounting element with the slot.

\* \* \* \* \*